United States Patent
Nagl et al.

(10) Patent No.: US 9,392,382 B2
(45) Date of Patent: Jul. 12, 2016

(54) MAGNET ARRANGEMENT FOR BONE CONDUCTION HEARING IMPLANT

(71) Applicant: Vibrant Med-El Hearing Technology GmbH, Innsbruck (AT)

(72) Inventors: Markus Nagl, Volders (AT); Thomas Lechleitner, Polling (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 161 days.

(21) Appl. No.: 13/933,490

(22) Filed: Jul. 2, 2013

(65) Prior Publication Data
US 2014/0012070 A1   Jan. 9, 2014
US 2016/0198270 A9   Jul. 7, 2016

Related U.S. Application Data

(63) Continuation-in-part of application No. 13/780,193, filed on Feb. 28, 2013.

(60) Provisional application No. 61/669,161, filed on Jul. 9, 2012.

(51) Int. Cl.
*H04R 25/00* (2006.01)
*A61N 1/375* (2006.01)
(Continued)

(52) U.S. Cl.
CPC  *H04R 25/60* (2013.01); *A61N 1/08* (2013.01); *A61N 1/36032* (2013.01); *A61N 1/375* (2013.01); *H04R 25/00* (2013.01); *A61N 1/3718* (2013.01)

(58) Field of Classification Search
CPC ........ H04R 25/00; H04R 25/60; A61N 1/375; A61N 1/36032; A61N 1/3718; A61N 1/08
USPC .......... 600/25; 381/98; 128/897–899; 607/57
See application file for complete search history.

(56) References Cited

U.S. PATENT DOCUMENTS 4,242,541 A * 12/1980 Ando ..................... H04R 9/047
                                                          381/182
7,566,296 B2 * 7/2009 Zimmerling ............. A61N 1/37
                                                          335/305

(Continued)

OTHER PUBLICATIONS

International Searching Authority, Authorized Officer Shane Thomas, International Search Report and Written Opinion—PCT/US13/49052, date of mailing Sep. 18, 2013, 22 pages.

*Primary Examiner* — Navin Natnithithadha
*Assistant Examiner* — Sunita Reddy
(74) *Attorney, Agent, or Firm* — Sunstein Kann Murphy & Timbers LLP

(57) ABSTRACT

An implantable magnetic transducer arrangement is described for a hearing implant in a recipient patient. An implant housing hermetically encapsulates an interior housing volume and is fixedly attached to skull bone beneath the skin of the patient. A magnetic transducer is located within the housing volume and includes multiple permanent magnets wherein adjacent magnets have opposite magnetic polarities, and one or more suspension elements that resiliently couple adjacent magnets to allow their relative movement. The magnetic transducer forms a coupled oscillating system with an external magnetic drive component above the skin of the patient to develop a mechanical stimulation signal to the implant housing for delivery by bone conduction of the skull bone as an audio signal to the cochlea of the patient.

3 Claims, 7 Drawing Sheets

(51) Int. Cl.
*A61N 1/08* (2006.01)
*A61N 1/36* (2006.01)
*A61N 1/37* (2006.01)

(56) References Cited

U.S. PATENT DOCUMENTS

| | | | |
|---|---|---|---|
| 2004/0012470 A1* | 1/2004 | Zimmerling | A61N 1/37 335/207 |
| 2005/0001703 A1* | 1/2005 | Zimmerling | B06B 1/045 335/220 |
| 2007/0100197 A1* | 5/2007 | Perkins | H04R 23/008 600/25 |
| 2009/0253951 A1* | 10/2009 | Ball | H04R 25/606 600/25 |
| 2010/0145135 A1* | 6/2010 | Ball | H04R 25/606 600/25 |
| 2011/0022120 A1* | 1/2011 | Ball | A61N 1/08 607/57 |
| 2011/0264172 A1* | 10/2011 | Zimmerling | A61N 1/36032 607/60 |

* cited by examiner

MAGNET ARRANGEMENT FOR BONE CONDUCTION HEARING IMPLANT

This application claims priority from U.S. Provisional Patent Application 61/669,161, filed Jul. 9, 2012, and from U.S. patent application Ser. No. 13/780,193, filed Feb. 28, 2013, which are incorporated herein by reference.

FIELD OF THE INVENTION

The present invention relates to medical implants, and more specifically to a novel transcutaneous auditory prosthetic implant system.

BACKGROUND ART

A normal ear transmits sounds as shown in FIG. 1 through the outer ear 101 to the tympanic membrane (eardrum) 102, which moves the ossicles of the middle ear 103 (malleus, incus, and stapes) that vibrate the oval window 106 and round window 107 membranes of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the cochlear nerve 105 reside. In response to received sounds transmitted by the middle ear 103, the fluid-filled cochlea 104 functions as a transducer to generate electric pulses which are transmitted to the cochlear nerve 105, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid or middle ear implant may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

Middle ear implants employ electromagnetic transducers to convert sounds into mechanical vibration of the middle ear 103. A transducer housing comprising a magnet assembly and a coil winding is attached to the ossicle bones within the middle ear 103 and microphone signal current is delivered to the coil winding to generate an electromagnetic field. The magnet vibrates in response to the interaction of the magnetic fields, causing vibration of the ossicle bones of the middle ear 103. See U.S. Pat. No. 6,190,305, which is incorporated herein by reference.

U.S. Patent Publication 20070191673 (incorporated herein by reference) described another type of implantable hearing prosthesis system which uses bone conduction to deliver an audio signal to the cochlea for sound perception in persons with conductive or mixed conductive/sensorineural hearing loss. An implanted floating mass transducer (FMT) is affixed to the temporal bone. In response to an externally generated electrical audio signal, the FMT couples a mechanical stimulation signal to the temporal bone for delivery by bone conduction to the cochlea for perception as a sound signal. A certain amount of electronic circuitry must also be implanted with the FMT to provide power to the implanted device and at least some signal processing which is needed for converting the external electrical signal into the mechanical stimulation signal and mechanically driving the FMT.

One problem with implantable hearing prosthesis systems arises when the patient undergoes Magnetic Resonance Imaging (MRI) examination. Interactions occur between the implant magnet and the applied external magnetic field for the MRI. The external magnetic field from the MRI may create a torque on the implant magnet, which may displace the magnet or the whole implant housing out of proper position and/or may damage the adjacent tissue in the patient. The implant magnet may also cause imaging artifacts in the MRI image, there may be induced voltages in the receiving coil, and hearing artifacts due to the interaction of the external magnetic field of the MRI with the implanted device.

Thus, for existing implant systems with magnet arrangements, it is common to either not permit MRI or at most limit use of MRI to lower field strengths. Other existing solutions include use of a surgically removable magnets, spherical implant magnets (e.g. U.S. Pat. No. 7,566,296), and various ring magnet designs (e.g., U.S. Patent Publication 2011/0022120). Among those solutions that do not require surgery to remove the magnet, the spherical magnet design may be the most convenient and safest option for MRI investigations even at very high field strengths. But the spherical magnet arrangement requires a relatively large magnet much larger than the thickness of the other components of the implant, thereby increasing the volume occupied by the implant. This in turn can create its own problems. For example, some systems, such as cochlear implants, are implanted between the skin and underlying bone. The "spherical bump" of the magnet housing therefore requires preparing a recess into the underlying bone. This is an additional step during implantation in such applications which can be very challenging or even impossible in case of very young children.

U.S. Patent Publication 20120029267 (incorporated herein by reference) describes an implantable hearing prosthesis having two planar implant magnets connected by a flexible connector member which is fixable to underlying skull bone. Each of the implant magnets is in the specific form of a center disk having magnetic polarity in one axial direction. Around the disk magnet is another ring magnet having an opposite magnetic polarity in a different direction. This ring/disk magnet arrangement has less magnetic interaction with an external magnetic field such as an MRI field.

SUMMARY

Embodiments of the present invention are directed to an implantable magnetic transducer arrangement for a hearing implant in a recipient patient. An implant housing hermetically encapsulates an interior housing volume and is fixedly attached to skull bone beneath the skin of the patient. A magnetic transducer is located within the housing volume and includes multiple permanent magnets wherein adjacent magnets have opposite magnetic polarities, and one or more suspension elements that resiliently couple adjacent magnets to allow their relative movement. The magnetic transducer forms a coupled oscillating system with an external magnetic drive component above the skin of the patient to develop a mechanical stimulation signal to the implant housing for delivery by bone conduction of the skull bone as an audio signal to the cochlea of the patient.

The magnets may include an inner cylindrical magnet, and at least one ring magnet concentrically outside the inner cylindrical magnet; and in some embodiments, there may be multiple ring magnets concentrically arranged outside the inner cylindrical magnet. In specific such embodiments, the suspension elements may include a spring membrane coupled to the cylindrical magnet on one side and coupled to the at least one ring magnet on the opposite side. Or the suspension elements may include a pair of spring membranes lying in parallel planes with the cylindrical magnet coupled to one of the spring membranes and the at least one ring magnet coupled to the other spring membrane.

Or the magnets may be pie-shaped segments connected by suspension elements to form a cylindrical disk. In specific such embodiments, each magnet may have the same size and shape, or the magnets may have different sizes and shapes.

Embodiments of the present invention also include a hearing implant system having an implantable magnetic transducer arrangement according to any of the foregoing.

DETAILED DESCRIPTION

Embodiments of the present invention are directed to an implantable MRI-compatible magnetic arrangement for a simple cheap and small-size mechanical transducer such as for a bone conduction hearing implant. The magnetic arrangement includes multiple permanent magnets wherein adjacent magnets have opposite magnetic polarities. One or more suspension elements (e.g. silicone, membrane, etc.) resiliently couple adjacent magnets to allow their relative movement. The resulting magnetic transducer thus forms a coupled oscillating system with an external magnetic drive component above the skin of the patient to develop a mechanical stimulation signal to the implant housing surrounding the magnets for delivery by bone conduction of the skull bone as an audio signal to the cochlea of the patient.

Figure 1:
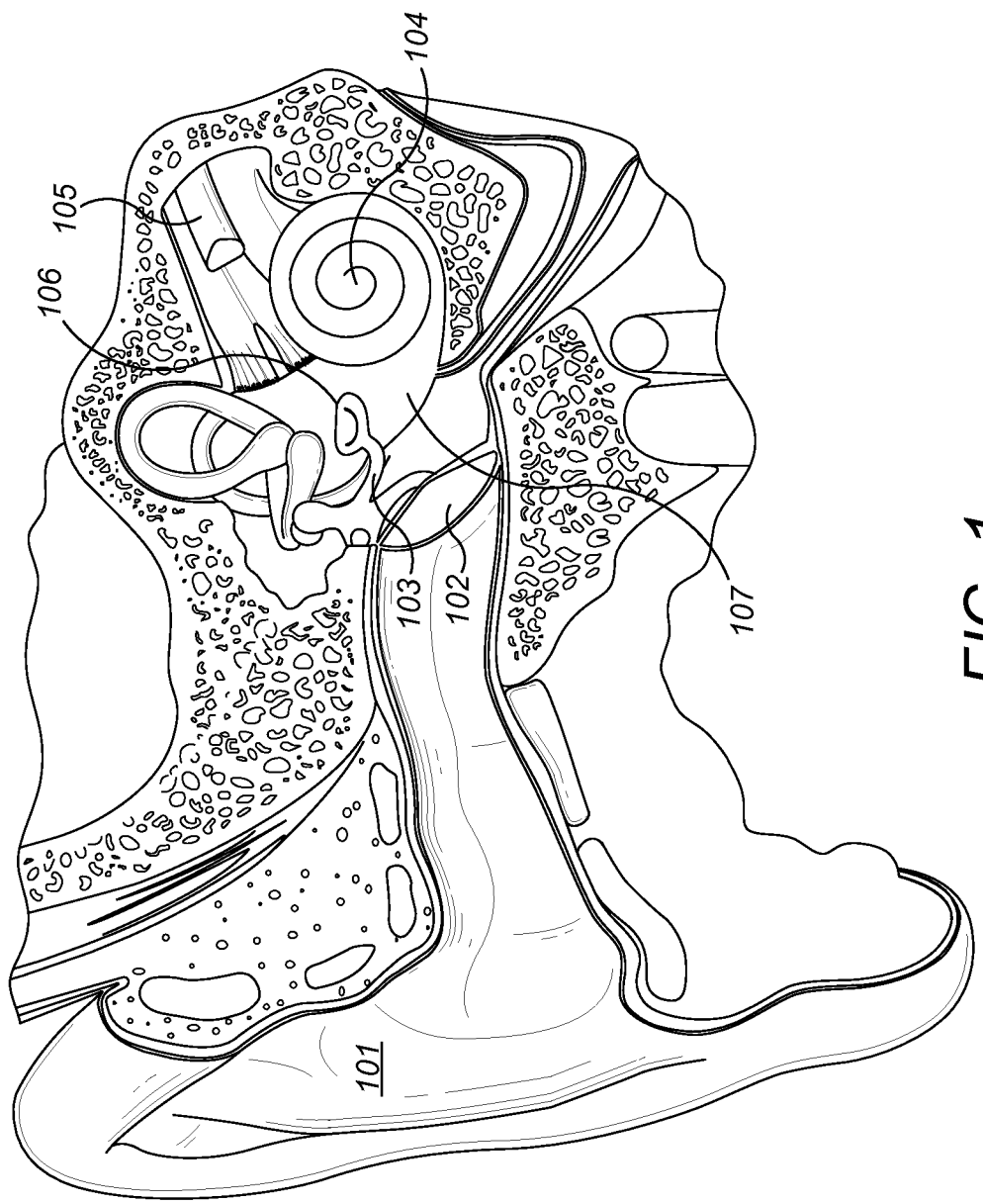
FIG. 1 shows anatomical structures of a typical human ear.
Figure 2A:
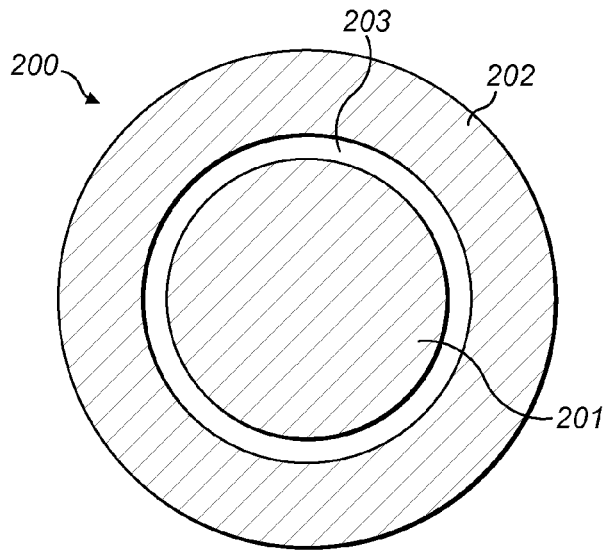
FIG. 2 A-B shows a top plant view and side cross-sectional view respectively of a magnetic arrangement for a hearing implant according to one specific embodiment of the present invention.
Figure 2B:
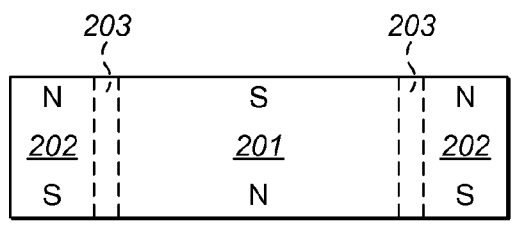

FIG. 2 A shows a top plant view and FIG. 2B shows a side cross-sectional view of a magnetic arrangement 200 for a hearing implant according to one specific embodiment. An inner cylindrical magnet 201 has a magnetic field polarity with the south magnetic pole on top and the north magnetic pole on the bottom. An outer ring magnet 202 fits concentrically outside around the inner cylindrical magnet 201 and has an opposite magnetic field polarity with the north magnetic pole on top and the south magnetic pole on the bottom. Spring membrane 203 (e.g., silicone material) acts as a suspension element that resiliently couples the inner cylindrical magnet 201 and the outer ring magnet 202 to allow their relative movement. The magnetic arrangement 200 is stable as soon as the magnets 201 and 202 are assembled and the restoring forces contribute to the forces from the spring membrane 203.

Figure 3:
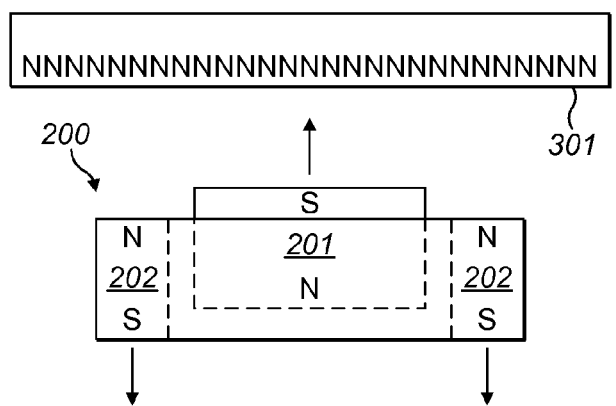
FIG. 3 shows the magnetic field from an external signal drive coil interacting with a magnet arrangement as shown in FIG. 2.
Figure 4A:
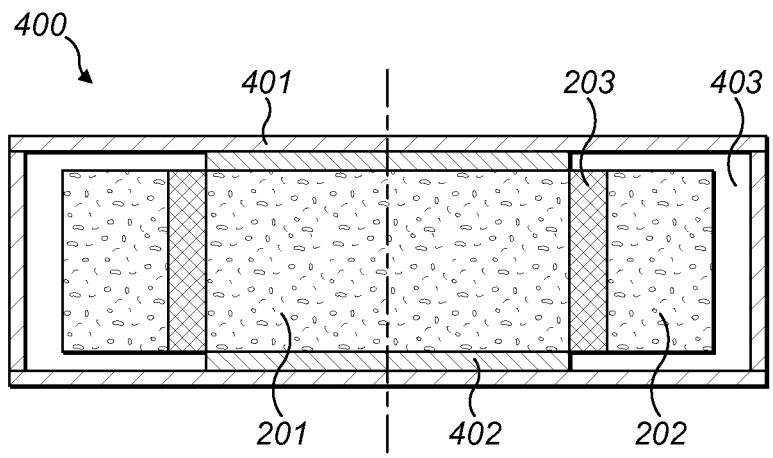
FIG. 4 A-D shows a magnetic transducer using a magnet arrangement according to an embodiment of the present invention.
Figure 4B:
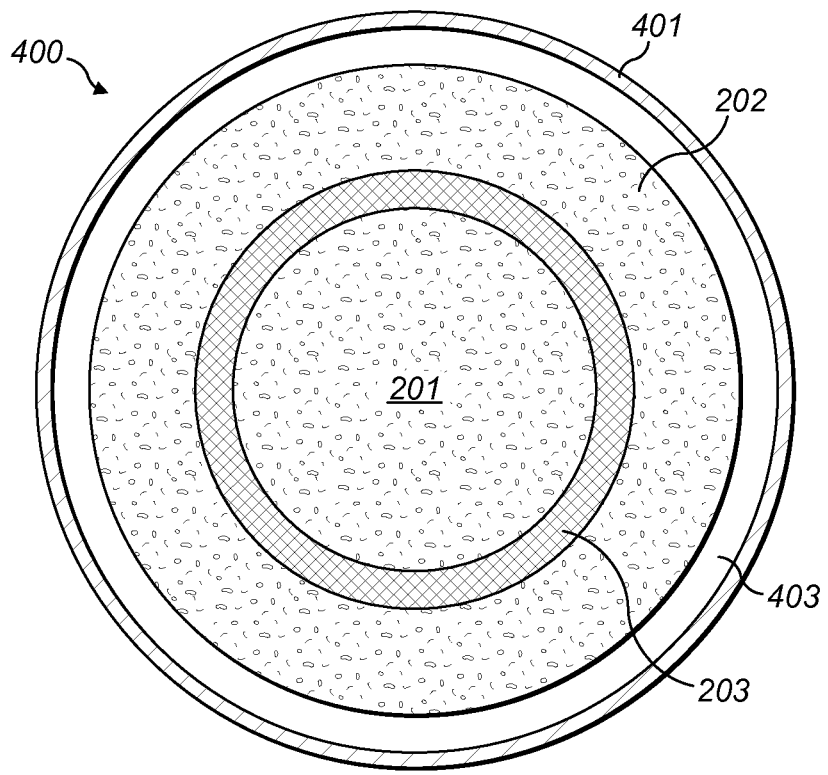
Figure 4C:
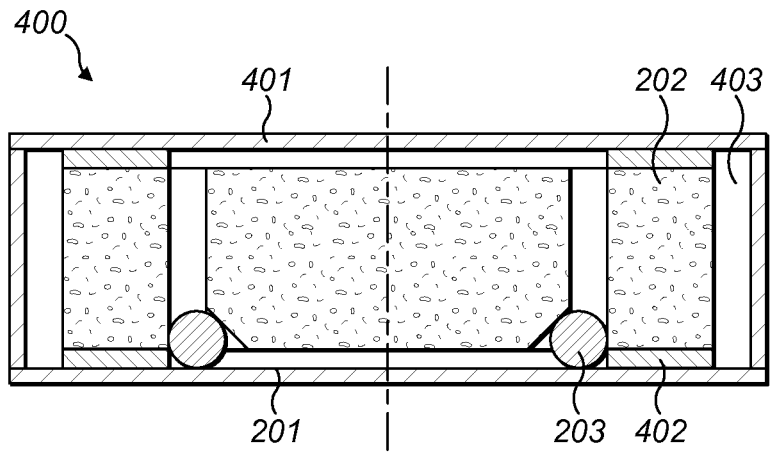
Figure 4D:
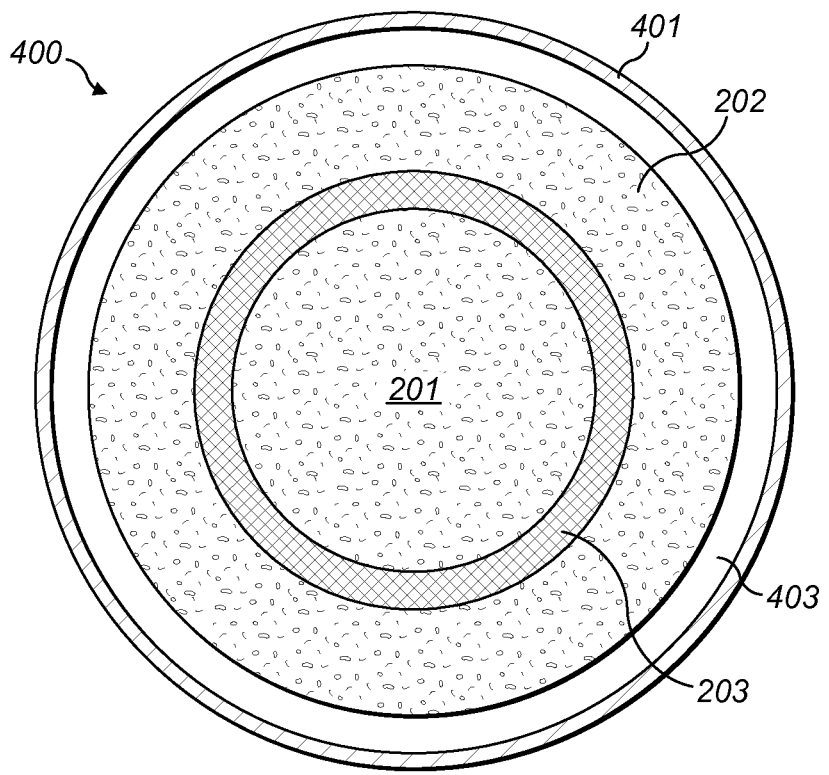

As shown in FIG. 3, the magnetic field from an external signal drive coil 301 causes the inner cylindrical magnet 201 and the outer ring magnet 202 to be displaced relative to each other in opposite directions. Geometric and volumetric construction characteristics of the magnets 201 and 202 affect the magnetic dipole moment to reduce/minimize torque on the arrangement caused by external magnetic field (e.g. MRI) such that:

$$m = V_1 H_1 - V_2 H_2 = 0$$

where m is the magnetic dipole moment, V is the volume of each magnet, and H is magnetic field strength of each magnet.

Such a magnetic arrangement also possesses a tunable frequency characteristic as a function of the elastic properties of the spring element 203 and the mass of the magnet arrangement 200. The suspension element spring membrane 203 critically contributes to the spring stiffness—e.g., soft silicone promotes a softer spring, harder silicone promotes a stiffer spring.

FIG. 4 A-D shows the above magnetic arrangement implemented as an implantable bone conduction transducer 400 enclosed within a hermetic housing 401. In such a transducer 400, the inner cylinder magnet 201, housing spacer 402, hermetic housing 401 and the patient skull act as one common mass. The outer ring magnet 202 vibrates suspended by the spring membrane 203 within the air gap 403 between the outer surface of the ring magnet 202 and the hermetic housing 401 in a push-pull configuration that is driven by the external magnetic field of the external signal drive coil 301. (Such operation is not limited to the specific form of external signal drive coil 301 as shown in FIG. 3). The external signal drive coil 301 excites a magnetic field such that the magnetic poles of the external coil arrangement that are opposite to the inner cylinder magnet 201 and outer ring magnet 202 each have opposing magnetic polarities. In another specific embodiment, the external signal drive coil 301 may include two or more coil assemblies. The bone conduction transducer 400 will equivalently work with the outer ring magnet 202, housing spacer 402 and hermetic housing 401 acting as a single common mass where the inner cylinder magnet 201 vibrates suspended by the spring membrane 203 within the outer ring magnet 202 as shown in FIG. 4C-D. The spring membrane 203 may be made of any elastic material (e.g., silicone) and may fill only a part or the entire gap between inner cylinder magnet 201 and outer ring magnet 202 as shown in FIGS. 4A and 4C. It may be useful if only one part is fixed at one end at a bevel on the inner cylinder magnet 201 by an o-ring suspension element/spring membrane 203. This may ease the manufacturing process and allow for easy alignment (i.e. centering) during assembly. The hermetic housing 401 does not require an electric or any other feed-through which is an advantage compared to conventional actively driven bone conduction devices.

In addition to its function as being a part of the magnetic driving system the inner cylinder magnet 201 also acts as the holding magnet for the external device. Ideally, the diameter of the outer device coincides with the diameter of the inner cylinder magnet 201 such that the external device is affected as little as possible by the vibrating outer ring magnet 202. But with regards to an external magnetic far field such as that from an MRI apparatus, the magnetic polarities of the internal magnets 201 and 202 oppose and are intended to cancel each other out. This net minimizing of the magnetic fields of the implant magnets reduces their magnetic interactions with the external MRI field to minimize adverse effects such as torque forces and imaging artifacts.

Such an implantable bone conduction transducer differs from the prior art in some important aspects. The implantable transducer has only passive implantable components and all the transducer functionality is in the implantable device itself; no prior art device takes advantage of this combination. Prior art transducers having only passive implantable components also utilize the skin acting as the spring element, with all the obvious disadvantages because the skin has poor elastic damping properties and if the magnetic forces are too strong, the skin may be traumatized or damaged.

Other prior art devices that do not rely on a separated attachment and transducer section (such as the Xomed Audiant) are likely to fail because the external device oscillates with such a large amplitude. Embodiments of the present invention provide considerably reduced oscillation amplitude of the external portion. This allows (but does not require) the attachment and transducer functionality to be located in the same component, but at the same time overcomes the shortcomings of the Audiant device.

Figure 5:
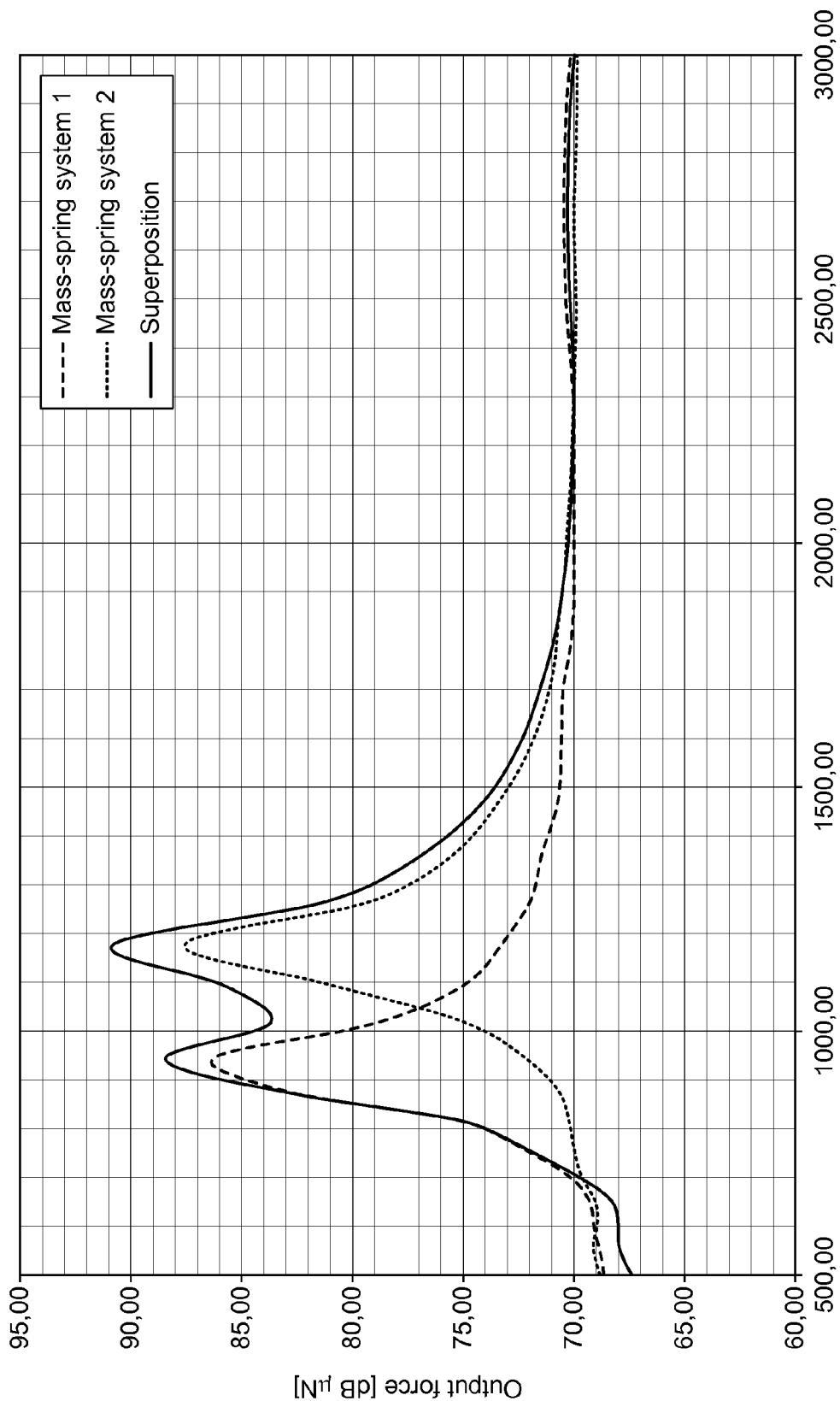
FIG. 5 is a graph of frequency vs. output force that shows that properly designing a spring system can achieve a frequency range optimal for speech understanding.

Embodiments of the present invention form a coupled oscillating system. One oscillator is the implantable arrangement of ring and disk magnet described above, and another oscillator includes a conventional external magnet, the skin and the implantable magnet arrangement as in the prior art. The first spring-mass system resonance frequency of the first implantable oscillator is determined by the mass of the vibrating magnet and the spring constant of the spring membrane 203. The second spring-mass system resonance frequency is determined by the mass of the vibrating magnet 201 or 202, the external portion and the skin acting as spring and damping element. One disadvantage of the prior art is, that the elastic properties of the skin cannot be exactly determined and also change somewhat over time, and the output force of the magnetic transducer arrangement 200 may become insufficient over the full frequency range for speech understanding. This is for example shown in FIG. 5. The output force of the bone conduction transducer drops quickly with frequencies that deviate only slightly from the resonance frequency. The coupled oscillator system allows the desired frequency range of resonance to be broadened by superimposing the resonance behavior of the two spring-mass systems. FIG. 5 shows a graph of output force over frequency showing that appropriate design of the spring systems enables achievement of a frequency range that is optimal for speech understanding.

Figure 6:
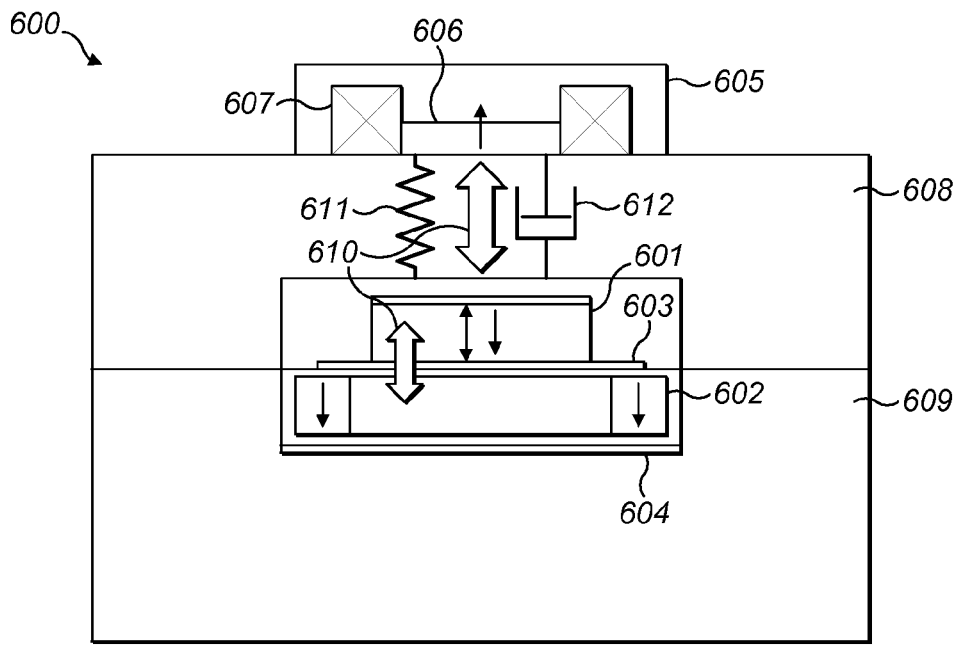
FIG. 6 shows an embodiment of the present invention together with the elastic spring functioning of the skin.

FIG. 6 shows another embodiment of the present invention along with symbolic elements for the spring and dampening functions of the patient's skin. Specifically, an implantable magnetic transducer arrangement 600 includes an implantable transducer housing 604 which is fixedly attached to the skull bone 609 beneath the skin 608 of an implanted patient. Within the transducer housing 604 is a spring membrane 603 that coupled on one side to a cylindrical magnet 601 and coupled on the other side to at least one ring magnet 602. In an alternative embodiment, both magnets 601 and 602 may be attached on the same side of the spring membrane 603. An external portion 605 is attached on the patient skin 608 over the transducer housing 604 by an attachment magnet 606 that is held in place by magnetic attraction to the implanted cylindrical magnet 601. A communication signal is sent through the external coil 607 that forms a dynamically changing coil magnetic field creating a coupled oscillator system 610 between the external portion 605, the magnet arrangement within the transducer housing 604, the skin spring function 611, and the skin damping function 612. The dynamic magnetic field of the external coil 607 alternately attracts and repels the cylinder magnet 601 that is coupled to the transducer housing 604 as vibration that acts as a mechanical stimulation signal to the skull bone 605 for bone conduction to the cochlea for perception as sound.

Figure 7:
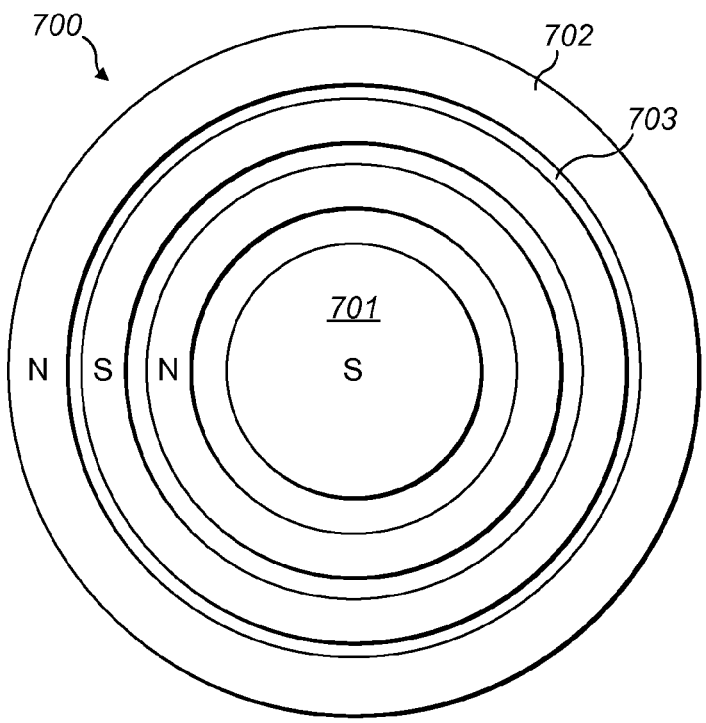
FIG. 7 shows an embodiment having multiple concentric ring magnets of alternating magnetic polarities.

Further embodiments may be implemented based on using a higher number of spring elements, which can lead to a further enlarged resonant frequency range. FIG. 7 one possible embodiment featuring an inner central cylinder magnet 701 and multiple concentric outer ring magnets 702 of alternating magnetic field polarities which are mounted on a connecting membrane spring suspension element 703 in a hermetic housing attached to the skull. The magnets 701 and 702 are deflected by a dynamic magnetic field signal from an external device. In such an arrangement, the individual suspension elements 703 between adjacent magnets may have different spring constants, which can allow for multiple different oscillation modes.

Figure 8:
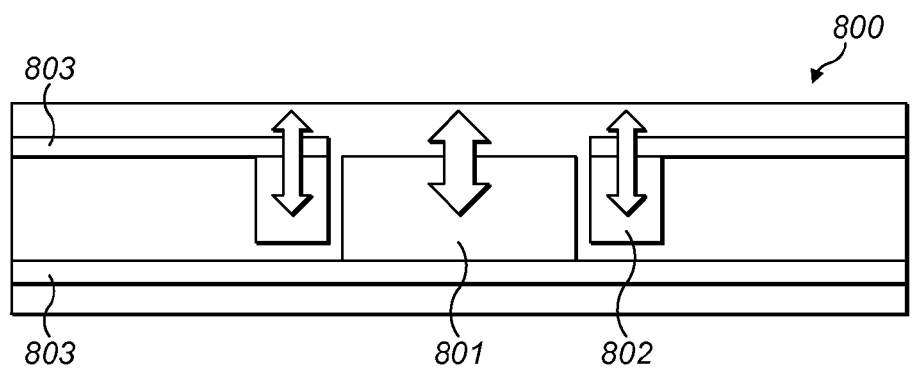
FIG. 8 shows an embodiment with two parallel spring membranes.

FIG. 8 shows another embodiment of an implantable magnetic transducer 800 having multiple suspension elements in the specific form of a pair of spring membranes 803 lying in parallel planes with the inner cylindrical magnet 801 coupled to one of the spring membranes 803 and an outer ring magnet 802 coupled to the other spring membrane 803. Again, the two different spring membranes 803 can be chosen to have different spring constants; for example, they may be made of different materials such as silicone, platinum, etc.

Figure 9:
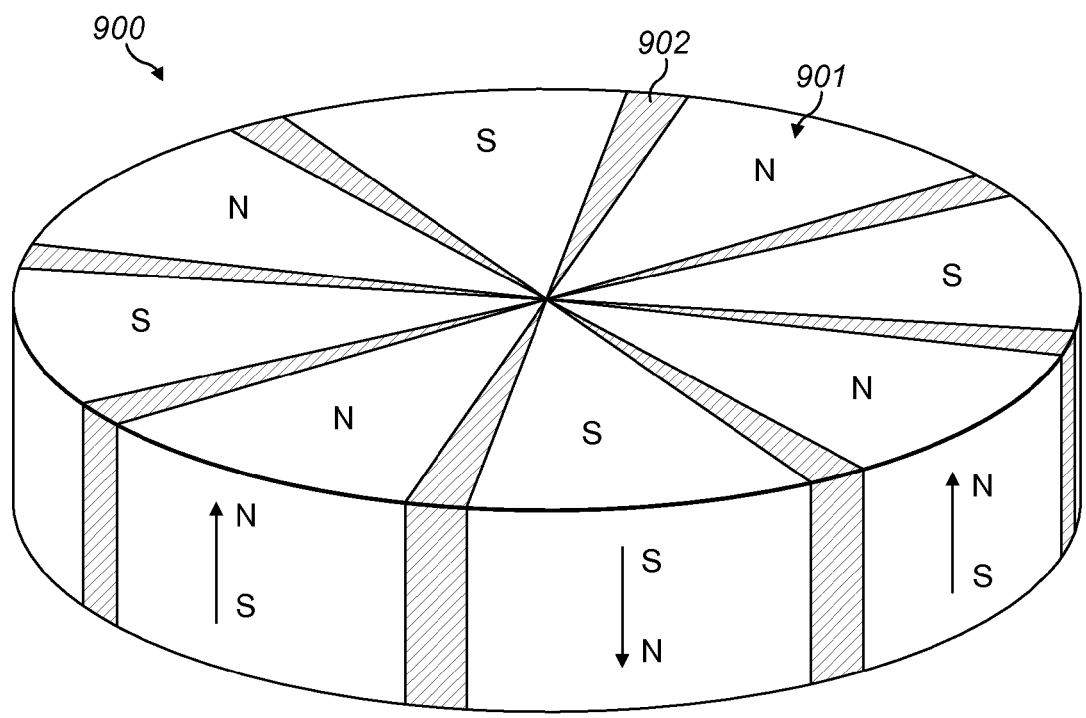
FIG. 9 shows an embodiment with multiple pie shaped sections connected by resilient suspension elements.

FIG. 9 shows another possible embodiment featuring a cylindrical magnet 900 divided into multiple individual pie shaped magnets 901 mounted on connecting suspension elements 902. Each pie-shaped magnet 901 may have the same size and shape, or they may have multiple different sizes and shapes. To control torque and provide tunable frequency characteristics the properties of the suspension elements 902 can be controlled (e.g. hard/soft silicone, etc.). Adjacent suspension elements 902 may be alternatingly soft and hard, thereby forming groups of pie-shaped magnets 901 between e.g. hard suspension elements 902 and having differing resonance frequencies. Adjacent pie shaped magnets 901 may have magnetic polarities in different directions, for example in opposite axial directions as shown in FIG. 9.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable magnetic transducer arrangement for a hearing implant in a recipient patient, the arrangement comprising:
   an implant housing hermetically encapsulating an interior housing volume and adapted to be fixedly attached to skull bone beneath the skin of the patient;
   a magnetic transducer within the housing volume having:
   i. a plurality of permanent magnets wherein adjacent magnets have opposite magnetic polarities;
   wherein the magnets include: an inner cylindrical magnet, and at least one ring magnet positioned concentrically outside the inner cylindrical magnet; and
   ii. one or more suspension elements configured for resilient coupling of adjacent magnets to allow movement between the adjacent magnets relative to each other;
   wherein the suspension elements include a spring membrane positioned between the inner cylindrical magnet and the at least one ring magnet, the spring membrane directly coupled to the cylindrical magnet on one side and directly coupled to the at least one ring magnet on the opposite side;

wherein the magnetic transducer is operatively coupled to an external magnetic drive component located above the skin of the patient;

wherein the magnetic transducer and the external magnetic drive component are configured to cooperate together to form an oscillating system that develops a mechanical stimulation signal to the implant housing for delivery by bone conduction of the skull bone as an audio signal to the cochlea of the patient.

2. A transducer arrangement according to claim 1, wherein at least one of the magnets interacts with an external holding magnet to affix the external drive coil in position on the skin of the patient.

3. A hearing implant system having an implantable magnetic transducer arrangement according to any of claim 1, or 2.

* * * * *